United States Patent
Hayakawa et al.

(10) Patent No.: US 9,132,070 B2
(45) Date of Patent: Sep. 15, 2015

(54) MANICURE COMPOSITION

(75) Inventors: Takayuki Hayakawa, Fujioka (JP); Masaaki Morita, Fujioka (JP)

(73) Assignee: MITSUBISHI PENCIL COMPANY, LIMITED, Tokyo (JP)

( * ) Notice: Subject to any disclaimer, the term of this patent is extended or adjusted under 35 U.S.C. 154(b) by 77 days.

(21) Appl. No.: 13/817,511

(22) PCT Filed: Aug. 30, 2011

(86) PCT No.: PCT/JP2011/069619
§ 371 (c)(1),
(2), (4) Date: Feb. 18, 2013

(87) PCT Pub. No.: WO2012/029791
PCT Pub. Date: Mar. 8, 2012

(65) Prior Publication Data
US 2013/0142854 A1  Jun. 6, 2013

(30) Foreign Application Priority Data

Aug. 30, 2010 (JP) ................................. 2010-192111
Aug. 29, 2011 (JP) ................................. 2011-185889

(51) Int. Cl.
*A61K 8/04* (2006.01)
*A61K 8/29* (2006.01)
(Continued)

(52) U.S. Cl.
CPC ... *A61K 8/04* (2013.01); *A61K 8/29* (2013.01); *A61K 8/33* (2013.01); *A61K 8/34* (2013.01); *A61K 8/8152* (2013.01); *A61K 8/894* (2013.01); *A61Q 3/02* (2013.01); *A61K 2800/412* (2013.01); *A61K 2800/413* (2013.01); *A61K 2800/5922* (2013.01)

(58) Field of Classification Search
None
See application file for complete search history.

(56) References Cited

U.S. PATENT DOCUMENTS

2005/0220731 A1* 10/2005 Ilekti et al. ............... 424/61
2007/0224136 A1*  9/2007 Dasgupta et al. ......... 424/59
(Continued)

FOREIGN PATENT DOCUMENTS

JP       4-103516 A    4/1992
JP     2003-507399 A   2/2003
(Continued)

OTHER PUBLICATIONS

Machine translation of JP 2006-321751 (2006).*
(Continued)

*Primary Examiner* — Bethany Barham
*Assistant Examiner* — Barbara Frazier
(74) *Attorney, Agent, or Firm* — Buchanan, Ingersoll & Rooney PC

(57) ABSTRACT

Provided is a manicure composition of a French nail type which has less disturbance of the lines brought about by a base color and a topcoat and is quickly dried, which does not cause dew condensation on the coating film under a moist environment for coating and has less leveling and less irregular color and which is excellent in a drying property, an adhesive property, flexibility, a masking property, a finished property, a discharge performance and a restirring property. The above manicure composition comprises at least ethanol and propylene glycol monomethyl ether as a solvent, titanium oxide A having an average primary particle diameter of 200 to 400 nm, titanium oxide B having an average primary particle diameter of 10 to 80 nm, an acrylic resin, polyether-modified polydimethylsiloxane and a plasticizer.

6 Claims, 2 Drawing Sheets

(51) Int. Cl.
*A61K 8/34* (2006.01)
*A61K 8/33* (2006.01)
*A61K 8/894* (2006.01)
*A61K 8/81* (2006.01)
*A61Q 3/02* (2006.01)

(56) References Cited

U.S. PATENT DOCUMENTS

2008/0121246 A1    5/2008   Saito et al.
2011/0033400 A1*   2/2011   Ehlis et al. ................. 424/60

FOREIGN PATENT DOCUMENTS

| JP | 2004-231554 A | 8/2004 |
| JP | 2005-154403 A | 6/2005 |
| JP | 2006-204332 A | 8/2006 |
| JP | 2006-296620 A | 11/2006 |
| JP | 2006-321751 A | 11/2006 |

OTHER PUBLICATIONS

International Search Report (PCT/ISA/210) issued on Nov. 29, 2011, by the Japanese Patent Office as the International Searching Authority for International Application No. PCT/JP2011/069619.

Notification of Transmittal of Copies of Translation of the International Preliminary Report on Patentability (Form PCT/IB/338 and PCT/IB/373) and the Written Opinion of the International Searching Authority (Form PCT/ISA/237) issued on Mar. 21, 2013, by the International Bureau of WIPO for International Application No. PCT/JP2011/069619. (8 pages).

* cited by examiner

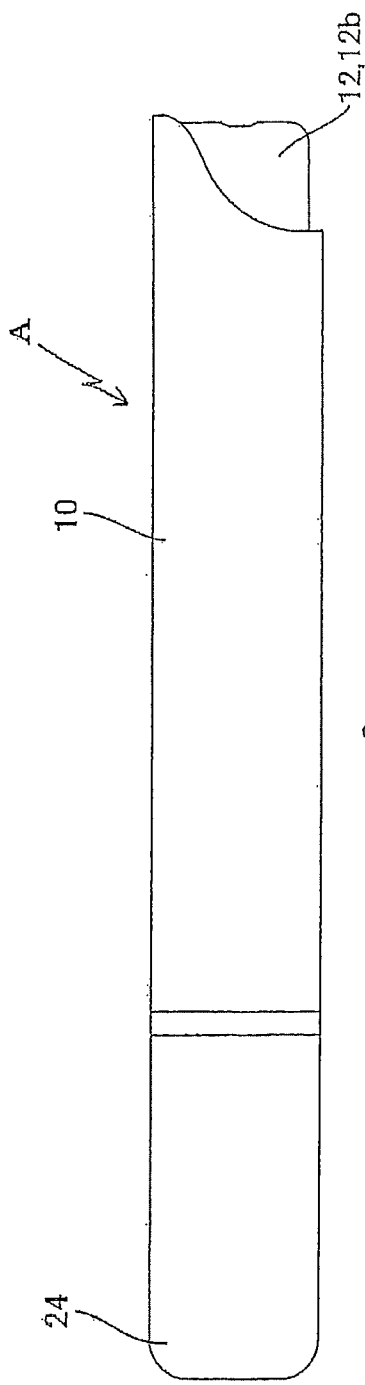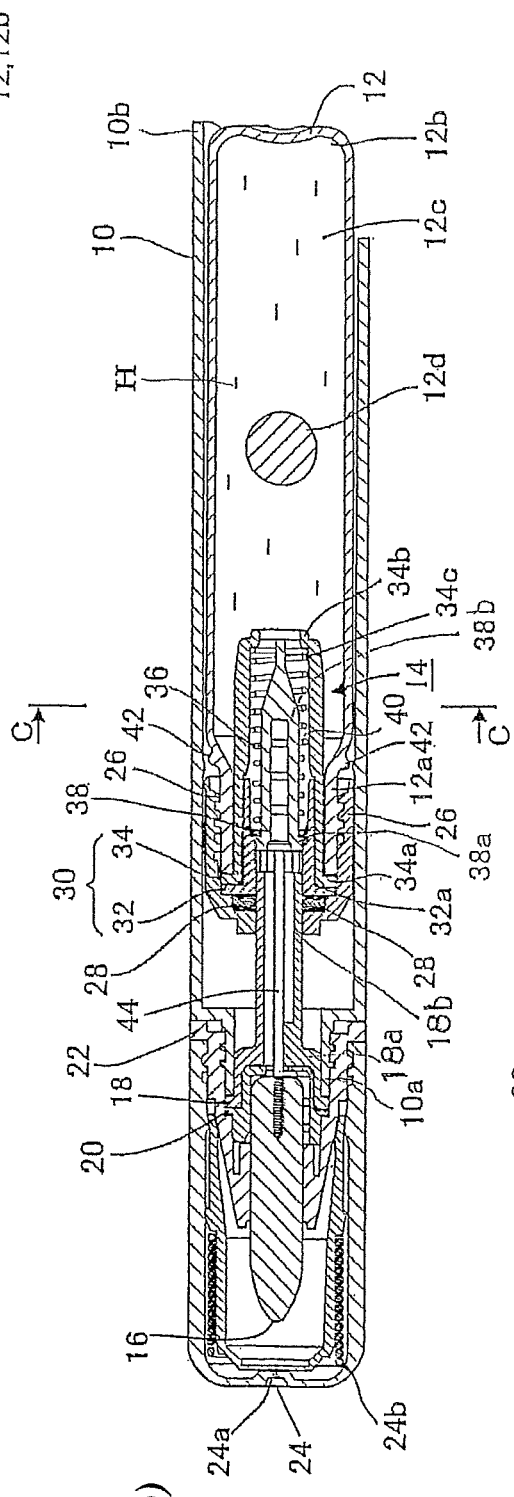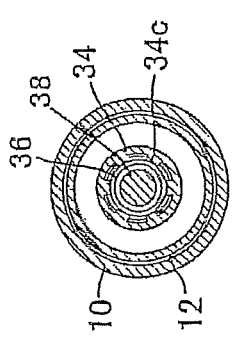
FIG. 1(a)
FIG. 1(b)
FIG. 1(c)

MANICURE COMPOSITION

TECHNICAL FIELD

The present invention relates to a manicure composition of a French nail type coated on an edge part of a nail in a so-called nail art painted in two different colors in which a nude color (translucent nail) is coated on a whole part of a nail and in which a white manicure is then coated on an edge part of a nail part.

BACKGROUND ART

In general, a manicure composition of a so-called French nail type in which a nude color (translucent nail) is coated on a whole part of a nail and in which a white manicure is then coated on an edge part of a nail is a white liquid prepared by mixing acetate esters as a solvent and nitrocelluloses as a resin to prepare a nail enamel liquid and mixing titanium oxide with the nail enamel liquid, and it is applied by a brush as is the case with conventional nail enamels.

Known as conventional manicure compositions of a French nail type and the like and applicators therefor are, for example, 1) manicure cosmetics for a nail art comprising at least one of nitrocellulose and alkid-1 as a film-forming agent, at least one of acetyl tributyl citrate, dibutyl phthalate and sucrose benzoate as a plasticizer and at least one of acetone, butyl acetate, methyl ethyl ketone, isopropanol, butanol, ethoxyethyl acetate and ethyl acetate as a solvent, wherein a main component of the solvent is the same as those of conventional nail enamel compositions, and the boundary line is shaded off by adding acetone and methyl ethyl ketone (refer to, for example, patent document 1), 2) manicures characterized by containing a specific alkylene oxide derivative and a film-forming agent in order to provide a manicure which is excellent in all of a health-maintaining function of a nail, a use feeling and a makeup retention, wherein aqueous nail enamels having a composition comprising water, an acryl base emulsion, an alcohol base solvent, titanium oxide and a defoamer are disclosed as the above manicures in Example 3-5 and Example 3-6 (refer to, for example, patent document 2), 3) aqueous compositions for cosmetic useful for nail enamels or hair-setting products, which contain an emulsion polymer having a minimum film-forming temperature MFT measured under the absence of a film-forming auxiliary agent and at least one glass transition temperature Tg of the dried film (provided that $35°$ C.$\leq Tg \leq 80°$ C. and $Tg-MFT \leq 8°$ C.), wherein an aqueous nail enamel having a composition comprising water, an acryl base emulsion, an alcohol base solvent and a silicone base solvent is disclosed as the above aqueous composition for cosmetic in Example 15 (refer to, for example, patent document 3), 4) applicators for a nail art characterized by that it is constituted from a rod-like main coating member which can occlude a liquid, a nail guide part for guiding an edge part of a nail onto the above main coating member and a nail enamel coating part which is connected with the nail guide part described above and in which a surface is formed in a planar form or a curved form are provided as applicators by which in enjoying drawing pictures on nails, lines having a fixed width can be drawn precisely and readily, as is the case with an occasion of particularly a French nail, on the nails regardless of a dominant hand (refer to, for example, patent document 4) and 5) adhesive seals for a French nail characterized by that they are prepared by a material provided with an adhesive property and an elasticity and formed in a thin and flat form and that they comprise a curved part formed thereon which corresponds to a smile line of a French nail and are stuck detachably on an edge part of a nail are known as an adhesive seal for a French nail which fits to the forms of nails of individuals and does not look unnatural as is the case with an artificial nail and which can finish readily a French nail in a short time (refer to, for example, patent document 5).

However, white compositions of conventional nail enamels including those shown in patent documents 1 to 3 described above have a high viscosity and are coated by a narrow brush, and therefore the existing situation is that a boundary line of two colors is not clearly recognized and that employed is a manner in which a French nail is coated after a nude color coated in an initial stage is completely dried and in which a topcoat is coated after the French nail is dried in order to improve a retention of the French nail.

In the above case, involved therein are the problems that when a base color and a topcoat are provided, the lines are blurred if they are not sufficiently dried since they have the same composition and that since the composition is coated by a narrow brush, the defect that the lines are not drawn well is brought about.

Further, the applicators for a nail art and the adhesive seals for a French nail which are described in the foregoing patent documents 4 and 5 are different in a technical idea from the present invention.

Patent document 1: Japanese Patent Application Laid-Open No. 231554/2004 (claims, examples and others)

Patent document 2: Japanese Patent Application Laid-Open No. 154403/2005 (claims, examples and others)

Patent document 3: Japanese Patent Application Laid-Open (through PCT) No. 507399/2003 (claims, examples and others)

Patent document 4: Japanese Patent Application Laid-Open No. 204332/2006 (claims, examples and others)

Patent document 5: Japanese Patent Application Laid-Open No. 296620/2006 (claims, examples and others)

DISCLOSURE OF THE INVENTION

In light of the problems on the conventional techniques described above and the existing situation, the present invention intends to solve them, and an object thereof is to provide a manicure composition of a French nail type which has less disturbance of the line brought about by a base color and a topcoat and is quickly dried, which does not cause dew condensation on the coating film even under a moist environment for coating and has less leveling and less irregular color and which is excellent in a drying property, an adhesive property, flexibility, a masking property, a finished property, a discharge performance and a restirring property.

In light of the conventional problems described above and the like, the present inventors intend to solve them, and they have found that a manicure composition which meets the object described above is obtained by containing at least ethanol and propylene glycol monomethyl ether as solvents, two kinds of titanium oxide having different ranges of an average primary particle diameter, an acrylic resin, polyether-modified polydimethylsiloxane and a plasticizer. Thus, the present invention have been come to complete.

That is, the present invention resides in the following items (1) to (4).

(1) A manicure composition comprising at least ethanol and propylene glycol monomethyl ether as solvents, titanium oxide A having an average primary particle diameter of 200 to 400 nm, titanium oxide B having an average primary particle diameter of 10 to 80 nm, an acrylic resin, polyether-modified polydimethylsiloxane and a plasticizer.

(2) The manicure composition as described in the above item (1), wherein assuming that a content of the titanium oxide A having an average primary particle diameter of 200 to 400 nm is 1, a blend ratio of the titanium oxide B having an average primary particle diameter of 10 to 80 nm is 0.5 to 1.5 in terms of a mass ratio.

(3) The manicure composition as described in the above item (1) or (2), wherein assuming that a content of propylene glycol monomethyl ether described above is 1, a blend ratio of ethanol is 1 to 50 in terms of a mass ratio.

(4) The manicure composition as described in any one of the above items (1) to (3), wherein a viscosity at a shear rate of 3.83 ($s^{-1}$) is 10 to 40 (mPa·s) at 25° C., and a viscosity at a shear rate of 383 ($s^{-1}$) is 10 to 30 (mPa·s).

According to the present invention, provided is a manicure composition of a French nail type which has less disturbance of the lines brought about by a base color and a topcoat and is quickly dried, which does not cause dew condensation on the coating film even under a moist environment for coating and has less leveling and less irregular color and which is excellent in a drying property, an adhesive property, flexibility, a masking property, a finished property, a discharge performance and a restirring property.

BRIEF DESCRIPTION OF THE DRAWINGS

In FIGS. 1, (a), (b) and (c) are an outside drawing, a vertical cross section and a lateral cross section along a C-C line which show one example of a manicure applicator storing therein the aqueous manicure composition of the present invention.

EXPLANATION of NUMERALS

Figure 2:
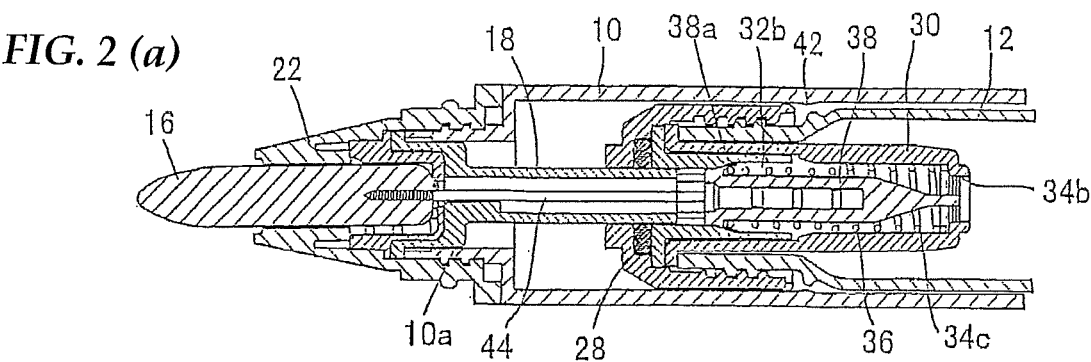
In FIG. 2, (a) to (d) are the explanatory drawings of the respective working steps in a valve mechanism of the manicure applicator shown in FIG. 1.
Figure 2:
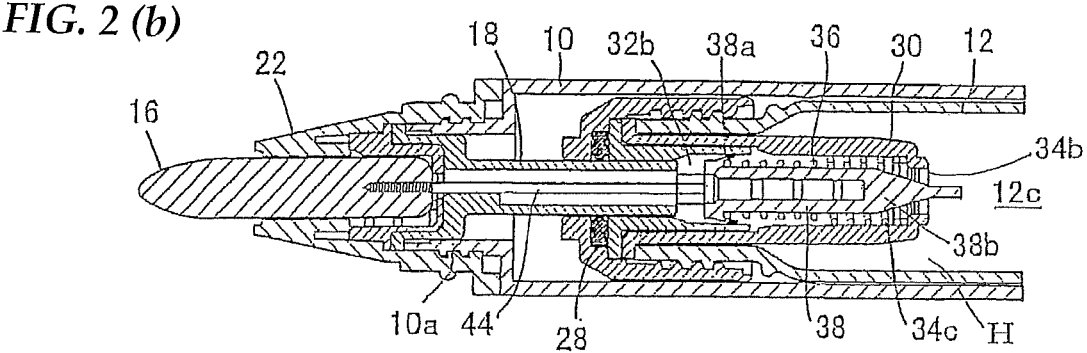
Figure 2:
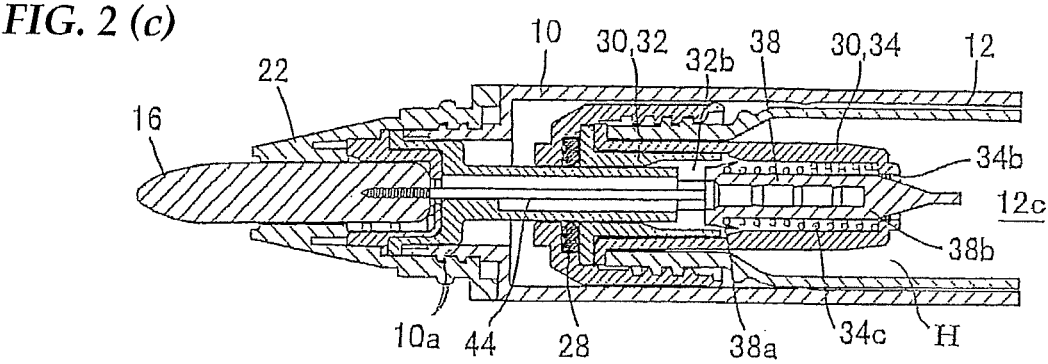
Figure 2:
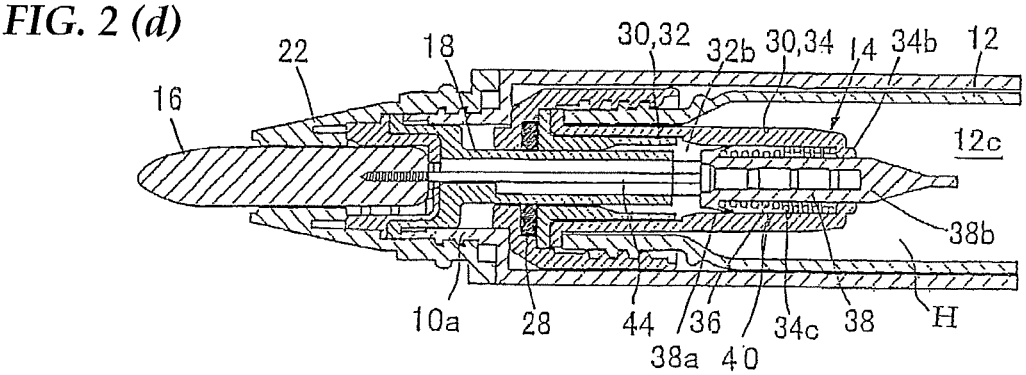

A Manicure applicator
H Manicure composition
10 Outer shaft
12 Inner shaft
14 Valve mechanism
16 Applying member DESCRIPTION of THE PREFERRED EMBODIMENTS The embodiments of the present invention shall be explained below in detail.

The manicure composition of the present invention is characterized by comprising at least ethanol and propylene glycol monomethyl ether as solvents, titanium oxide A having an average primary particle diameter of 200 to 400 nm, titanium oxide B having an average primary particle diameter of 10 to 80 nm, an acrylic resin, polyether-modified polydimethylsiloxane and a plasticizer.

Ethanol and propylene glycol monomethyl ether are used in combination as the solvent used in the present invention. In the present invention, acetate esters and water are not added, and ethanol and propylene glycol monomethyl ether are used in combination, whereby a disturbance of the line brought about by a base color and a topcoat is reduced. Also, capable of being prevented is the defect that when ethanol is used alone as the solvent, dew condensation is brought about on the coating film under a moist environment for coating.

A content of propylene glycol monomethyl ether used is preferably 1 to 40% by mass based on a total amount of the manicure composition, and a content of ethanol is preferably 1 to 60% by mass based on a total amount of the manicure composition. If a content of propylene glycol monomethyl ether exceeds 40% by mass, the drying property becomes worse and complicated, and therefore it is not preferred.

From the viewpoints that a disturbance of the lines brought about by a base color and a topcoat is further reduced and that the composition is quickly dried (quick drying), assuming that a content of propylene glycol monomethyl ether is 1, a blend ratio of ethanol is preferably 1 to 50 (1:1 to 1:50) in terms of a mass ratio. Combined use of the solvents falling in the above blend range makes it possible to dry the manicure composition of the present invention more quickly than conventional nail enamel compositions using a solvent such as ethyl acetate and butyl acetate.

In particular, from the viewpoint that an effect exerted by combined use of the solvents according to the present invention is exhibited to a maximal degree, a blend ratio of propylene glycol monomethyl ether to ethanol is preferably 1:1 to 1:10 in terms of a mass ratio.

Two kinds of titanium oxides having different ranges of an average primary particle diameter are used as titanium oxide used in the present invention, and the titanium oxide A having an average primary particle diameter of 200 to 400 nm as one titanium oxide and the titanium oxide B having an average primary particle diameter of 10 to 80 nm as the other titanium oxide are used in combination.

Combined use of the above titanium oxides A and B having different ranges of an average primary particle diameter makes it possible to reduce leveling and irregular color and exert an excellent masking property and an excellent finished property more than each single use of the titanium oxide A or B. That is, the titanium oxide B alone having an average primary particle diameter of 10 to 80 nm scatters less light and has less whiteness degree, but it assumes a form of an aggregation state and is reduced in irregular color (whiteness degree) and improved in leveling by mixing with conventional titanium oxide having an average primary particle diameter of 200 to 400 nm. Also, use of titanium oxide in which an average primary particle diameter falls outside a range of 10 to 80 nm or outside a range of 200 to 400 nm makes it impossible to exert the effects of the present invention.

In the present invention (including examples described later), the "average primary particle diameter" means a particle diameter determined by transmission electron microscopic image analysis.

The titanium oxide A having an average primary particle diameter of 200 to 400 nm which can be used includes, to be specific, at least one of CR-50 and CR-60 (each manufactured by Ishihara Sangyo Co., Ltd.), JR-800 and JR-301 (each manufactured by TAYCA CORPORATION), UNIPURE WHITE LC 987 (manufactured by LCW Inc.) and KEMIRA 402 (manufactured by KEMIRA Inc.), and the titanium oxide B having an average primary particle diameter of 10 to 80 nm includes, to be specific, at least one of TTO-55(A) and TTO-51(A) (each manufactured by Ishihara Sangyo Co., Ltd.) and MT-100TV and MT-500B (each manufactured by TAYCA CORPORATION).

A content of the titanium oxide A used is preferably 1 to 20% by mass based on a total amount of the manicure composition, and a content of the titanium oxide B is preferably 0.5 to 20% by mass based on a total amount of the manicure composition.

From the viewpoints of reducing further leveling and irregular color and exerting further an excellent masking property and an excellent finished performance, assuming that a content of the titanium oxide A is 1, a blend ratio of the titanium oxide B is preferably 0.1 to 5 (1:0.1 to 1:5), more preferably 0.5 to 1.5 (1:0.5 to 1:1.5) in terms of a mass ratio.

In the present invention, if a content of the titanium oxide A is too high in excess of 20% by mass, irregular color is liable to be caused. On the other hand, if it is less than 1% by mass, it results in a reduction of the masking property and therefore is not preferred.

The acrylic resin used in the present invention functions as a coating film-forming agent and a dispersion stabilizer. To be specific, at least one of alkyl acrylate copolymers, alkyl acrylate.styrene copolymers and the like can be contained, and from the viewpoint of the dispersion stability and the coating film performance, the alkyl acrylate copolymers are preferably used.

A content of the above acrylic resins is 1 to 20% by mass, preferably 5 to 15% by mass based on a total amount of the manicure composition.

If a content of the acrylic resins is less than 1% by mass, the manicure composition loses an adhesive property with a base and is inferior in finishing, and it is deteriorated as well in a restirring property. On the other hand, if it exceeds 20% by mass, the manicure composition is increased in a viscosity and inferior in a discharge performance, and it is deteriorated as well in finishing. Accordingly, both are not preferred.

The polyether-modified polydimethylsiloxane used in the present invention is added from the viewpoints that a French liquid is prevented from moving to a boundary part of a line generated in a case of solvents having a high volatility which is constituted from ethanol and propylene glycol monomethyl ether as the solvents and that the coating film is uniformized.

The polyether-modified polydimethylsiloxane which can specifically be used includes at least one of SH3775M and SH3749 (manufactured by Dow Corning Toray Co., Ltd.), KF6017 and KF6013 (manufactured by Shin-Etsu Silicone Co., Ltd.) and the like.

A content of the above polyether-modified polydimethylsiloxanes is 0.0001 to 1% by mass, preferably 0.001 to 0.1% by mass based on a total amount of the manicure composition.

If a content of the above polyether-modified polydimethylsiloxanes is less than 0.0001% by mass, an effect for addition of the polyether-modified polydimethylsiloxane is reduced. On the other hand, if it exceeds 1% by mass, the finishing is deteriorated.

The plasticizer used in the present invention is used as a plasticizer for the coating film, and it includes, for example, at least one of acetyl triethyl citrate, acetyl tributyl citrate, diisopropyl sebacate and the like.

A content of the above plasticizers is 0.5 to 10% by mass, preferably 1 to 5% by mass based on a total amount of the manicure composition.

If a content of the above plasticizers is less than 0.5% by mass, the coating film is too hardened and therefore fragile. On the other hand, if it exceeds 10% by mass, the drying time is too long and the coating film is softened. Accordingly, both are not preferred.

The manicure composition of the present invention has preferably a viscosity of 10 to 40 (mPa·s) at a shear rate of 3.83 ($s^{-1}$) and a viscosity of 10 to 30 (mPa·s) at a shear rate of 383 ($s^{-1}$) in measurement of the viscosity by means of a corn plate type viscometer at a temperature of 25° C.

Allowing the manicure composition to fall in the respective viscosity ranges described above at the above prescribed shear rates makes it possible to allow the manicure composition of the present invention to flow from a so-called pen feed prepared by fixing fibers with resins and the like or fusing fibers, makes it possible to coat the manicure composition in the same manner as coating by a marker, reduces a fluctuation of the coated area which is brought about by power adjustment as is the case with coating by a fine brush and make it easy to draw and paint lines. Accordingly, the manicure composition is readily coated without using conventional applicators in which a complicated step part is formed as described in patent document 4 and the like.

If a difference in the viscosity at 25° C. between the shear rates of 3.83 ($s^{-1}$) and 383 ($s^{-1}$) is 10 times or more, the manicure composition is less liable to be impregnated into the applying member and is deteriorated in usability.

Also, the viscosity described above can be controlled by combining the titanium oxides A and B having different average primary particle diameters, the acrylic resin, the polyether-modified polydimethylsiloxane, the plasticizer and the solvents used in combination so that suitable contents are obtained.

The manicure composition of the present invention can suitably contain, in addition to the respective components described above, pigments such as Red No. 201, No. 202 and No. 220, Yellow No. 4 AL Lake, navy blue, and red iron oxide, pearl pigments and other shiny pigments for the purpose of color change other than a white color on an edge part of a nail as long as the effects of the present invention are not damaged. Also, the manicure composition can suitably contain nitrocellulose, an acrylic resin and the like as a dispersant as long as the effects of the present invention are not damaged.

The manicure composition of the present invention can be prepared by mixing and dispersing the respective components described above in contents falling in the ranges described above by means of a mixing disperser such as, for example, a bead mill, a homomixer, a disper, an attriter, a ball mill, and a sand grinder.

The manicure composition of the present invention thus constituted is received in a manicure applicator constituted from a bottle (vessel) receiving therein the manicure composition of the present invention and a brush which is an applying member mounted in a cap and a manicure applicator which is equipped with at least a liquid-storing space for storing a manicure composition and an applying member of a so-called pen feed type prepared by fixing fibers with resins and the like or fusing fibers and in which the liquid is transported from the liquid-storing space described above to the applying member by a capillary force, wherein the manicure composition is received in the liquid-storing space and can suitably be used.

The manicure composition applicator which can be used includes, for example, a manicure composition applicator A shown in FIG. 1 in which the manicure composition having the constitution described above is stored. In FIGS. 1, (a), (b) and (c) are an outside drawing of the manicure composition applicator A, a vertical cross section thereof and a lateral cross section thereof along a C-C-line, and in FIG. 2, (a) to (d) are the explanatory drawings of the respective working steps in a valve mechanism of the manicure applicator A shown in FIG. 1.

In the above manicure applicator A, a tank-like inner shaft 12 is movably arranged, as shown in FIG. 1 and FIG. 2, in an approximately cylindrical outer shaft 10 in which a rear end part 10b is opened, and knocking the rear end part 12b of the inner shaft 12 by the user allows the inner shaft to move forward versus the outer shaft 10 and allows a valve mechanism 14 described later to work to supply the manicure composition. H of the present invention to an applying member 16 mounted in a tip part 10*a* of the outer shaft 10.

The tip part 10*a* of the outer shaft 10 is tapered in a step form, and an outer circumference (spreading in a flange form) of a cup-like tip part 18*a* of a manicure-introducing tube (a conduit for allowing the manicure composition H to flow from the valve mechanism 14 to an applying member 16 side) 18 is brought into contact with a front surface of the tip part 10*a*. A rear part of the applying member 16 is inserted into the tip part 18*a* of the manicure-introducing tube 18 via a seal ring 20. In a state in which the seal ring 20 and the tip part 18*a* of the manicure-introducing tube 18 described above are allowed to insert through a hollow part of a hollow and tapered cylindrical front shaft 22 from a central part of the applying member 16 described above, the above front shaft 22 is externally fitted to the tip part 10*a* of the outer shaft described above, whereby the applying member 16, the seal ring 20 and the tip part 18*a* of the manicure-introducing tube are fixed to the outer shaft 10. A cap 24 for masking the applying member 16 to protect it is detachably externally fitted to the tip part 10*a* of the outer shaft, and the cap 24 is provided so that an inside inner cap 24*a* presses the above front shaft 22 by virtue of a spring 24*b*.

The inner shaft 12 described above is closed in the rear end part 12*b*, and a liquid-storing space 12*c* for storing the applying member 16 is formed in an inside thereof (a stirring ball 12*d* is received therein in a certain case). On the other hand, the valve mechanism 14 is fixed by an inner front shaft 26 in a state in which the valve mechanism 14 described above is installed in a front end part (a tip part of the inner shaft) 12*a*. To be specific, the rear end part 18*b* of the manicure-introducing tube 18 is slidably connected with the valve mechanism 14 in a state in which the valve mechanism 14 is installed in the front end part 12*a* formed by tapering a front side of the inner shaft 12, and a packing 28 is disposed in a front end part of the valve mechanism 14 to fix the inner front shaft 26 to the front end part 12*a* of the inner shaft by screwing and the like.

In this connection, in the valve mechanism 14, a valve sheet member 30 and a valve rod member 38 relatively move toward a shaft direction in the middle of a communicating passage between the liquid-storing space 12*c* for storing the manicure composition H and the applying member 16, whereby supplying the manicure composition H to the applying member 16 is allowed or prevented. The valve sheet member 30 of the valve mechanism 14 is an approximate cylinder in which apertures are provided in both end parts in a shaft direction, and liquid-seal parts brought into sliding contact with the valve rod are formed in a front side (front side valve member 32) and a rear side (rear side valve member 34) in an inside thereof. The aperture of the rear side described above is provided facing on the liquid-storing space 12*c*, and the aperture of the front side is provided facing on the applying member 16. Also, guiding poles 34*c* for guiding the valve rod member 38 which are protruded from an inner wall part to a diameter central direction are formed, as shown in FIG. 1 (*b*), in a rib form from an approximate center of a longitudinal direction through a rear side on an inner wall part of the rear side valve member 34 in the valve sheet member 30. The above guiding poles 34*c* can prevent the valve rod member 38 from being inclined by a shock when the outer shaft 10 falls and running onto an end face of the front side valve member 32 to bring about inferior knocking. To be specific, the front side valve member 32 assumes wholly an approximately cylindrical form in which a flange 32*a* is enlarged in a diameter in a front end and in which a rear side inner circumferential face is enlarged more in a diameter than a front side inner circumferential face, and the above rear side inner circumferential face corresponds to a front side liquid-tight seal part 32*b* shown in FIGS. 2 (*a*) and (*b*). Also, the rear side valve member 34 assumes an approximately cylindrical form in which a flange 34*a* is enlarged in a diameter in a front end and in which a rear side end is stepwise reduced in a diameter and opened, and the above inner circumferential face of the diameter-reduced part corresponds to a rear side liquid-seal part 34*b*. In a state in which the front side valve member 32 is concentrically inserted into the rear side valve member 34 from a front side thereof and superposed thereon, the flanges 32*a* and 34*a* are superposed. In a state in which the packing 28 is further superposed on a front thereof, they are covered with the inner front shaft 26, and the inner front shaft 26 is fixed to the inner shaft front end part 12*a* by screwing. Incidentally, a front face of the diameter-reduced part at a rear side end of the rear side valve member 34 is a part for accepting a spring member 36 described later.

The valve rod member 38 described above is movably received in a hollow part of the front side valve member 32 and the rear side valve member 34. Provided respectively in an outer circumferential part of the valve rod member 38 are a piston part 38*a* of a front side brought into sliding contact with the front side liquid-seal part 32*b* of the front side valve member 32 in the valve sheet member 30 in a liquid-seal state and a piston part 38*b* of a rear side brought into sliding contact with the rear side liquid-seal part 34*b* of the rear side valve member 34 in the valve sheet member 30 in a liquid-seal state, and a space 40 through which the manicure composition H flows is provided between an outer circumferential part almost in a central part of the above valve rod member 38 and an inner face of the valve sheet member 30 described above. To be specific, an umbrella-like flexible flange which is enlarged in a diameter is formed in the piston part 38*a* at a front side of the valve rod member 38. Also, the piston part 38*b* of a rear side is formed on a smooth outer circumferential face in a rear attenuation form, and it is constituted so that when the valve rod member 38 moves backward, a central part thereof having a large diameter moves slidingly while brought into close contact with the rear side liquid-seal part 34*b* of the rear side valve member 34 after a rear end part of the valve rod member 38 having a small diameter passes through an aperture of the rear side valve member 34.

As described above, the spring member 36 is interposed between the valve sheet member 30 and the valve rod member 38 in the valve mechanism 14, and the spring member 36 is brought into contact with the piston part 38*a* at a front side of the valve rod member 38 from the rear to push the piston part so that it is positioned at a front side end versus the valve sheet member 30. Accordingly, when a pressing force is not applied by knocking a rear end of the inner shaft 12, the piston part 38*a* at a front side is positioned, as shown in FIG. 1 (*b*) and FIGS. 2 (*a*) and (*b*), so that it is brought into internal contact with a tip of the front side liquid-seal part 32*b* by the spring member 36. The inner front shaft 26 is brought into contact with a circular projection 42 in the outer shaft 10 to prevent the inner shaft 12 from moving further toward the rear and coming out.

Also, a rear end part 18*b* of the manicure-introducing tube (conduit) 18 for communicating a front side aperture (a tip side aperture of the front side valve member 32) with the applying member 16 is inserted into the above front side aperture, and a guiding rod member 44 for guiding the manicure composition H to the applying member 16 is inserted into the above manicure-introducing tube 18. A gap between the guiding rod member 44 and an inner face of the manicure-introducing tube 18 is provided with a dimension in which the manicure composition H is guided. In respect to a positional relation of the guiding rod member 44 with the manicure-introducing tube 18, the guiding rod member 44 is supported by plural ribs, though not illustrated, which are formed in an inside of a tip part 18a side of the introducing tube 18 so that the guiding rod member 44 is positioned in a center in a diameter direction of the manicure-introducing tube 18, whereby looseness in the diameter direction is cancelled. Also, a tip part of the guiding rod member 44 is inserted into a rear part of the applying member 16.

In the valve mechanism 14 of the manicure applicator A having the above form, a distance between the piston part 38a at a front side of the valve rod member 38 and the piston part 38b at a rear side thereof is set shorter than a distance between the front side liquid-seal part 32b and the rear side liquid-seal part 34b in the valve sheet member 30 described above. That is, the valve mechanism 14 is formed so that a first state in which the piston part 38a at a front side of the valve rod member 38 is brought into sliding contact with the front side liquid-seal part 32b in the valve sheet member 30, a second state in which the piston part 38a at a front side of the valve rod member 38 and the piston part 38b at a rear side thereof are not brought into sliding contact with both liquid-seal parts in the valve sheet member 30 and a third state in which the piston part 38b at a rear side of the valve rod member 38 is brought into sliding contact with the rear side liquid-seal part 34b in the valve sheet member 30 can be assumed by allowing the valve sheet member 30 and the valve rod member 38 to relatively move.

In the manicure applicator A constituted in the manner described above, the spring member 36 is brought, as shown in FIG. 2 (a), into contact with the piston part 38a at a front side of the valve rod member 38 from the rear in a standard state (non-knocking state) in which the inner shaft rear end part 12b is not knocked by the user, and the spring member 36 is provided so that it is positioned at a front side end versus the valve sheet member 30. In a state in which knocking of the inner shaft rear end part 12b is initiated, the valve rod member 38 moves, as shown in FIG. 2 (b), from the position of the front side end to the rear at less than a first distance versus the valve sheet member 30 as is the case with the first state described above, wherein the piston part 38a at a front side of the valve rod member 38 is brought into sliding contact with the front side liquid-seal part 32b of the valve sheet member 30 while brought into tight contact therewith, and assumed is a state in which the piston part 38b at a rear side of the valve rod member 38 is apart from the rear side liquid-seal part 34b of the valve sheet member 30 to pressurize a liquid-storing space 12c side. In the above case, the piston part 38b at a rear side of the valve rod member 38 is apart from the rear side liquid-seal part 34b of the valve sheet member 30, but the piston part 38a at a front side of the valve rod member 38 is brought into sliding contact with the front side liquid-seal part 32b of the valve sheet member 30 while brought into tight contact therewith, and therefore a state in which the manicure composition H does not blow out even when an internal pressure of the liquid-storing space 12c is elevated is assumed. Further, in a state in which the inner shaft rear end part 12b is continuously knocked, the valve rod member 38 moves, as shown in FIG. 2 (c), to the rear at the first distance or more and less than a second distance versus the valve sheet member 30 as is the case with the second state described above, and the piston part 38a at a front side of the valve rod member 38 is separated from the front side liquid-seal part 32b of the valve sheet member 30. In the above case, assumed is a state in which the piston part 38b at a rear side of the valve rod member 38 is apart from the rear side liquid-seal part 34b of the valve sheet member 30 and in which a front side aperture thereof is connected with a rear side aperture thereof through an inside of the valve sheet member 30. The manicure composition H tends to blow out to an applying member side when an inner pressure is elevated, but since the applicator is communicated with the atmosphere as shown above, a timing of assuming the above state is a moment in the pressing operation, and the manicure composition H does not blow out. Further, the liquid-storing space 12c is improved in an air-replacing property. Also, the manicure composition H flows out to an applying member 16 side passing through the guiding rod member 44. In a state in which the inner shaft rear end part 12b is further continuously knocked, the valve rod member 38 moves, as shown in FIG. 2 (d), to the rear side at the second distance or more versus the valve sheet member 30 as is the case with the third state described above, wherein the piston part 38a at a front side of the valve rod member 38 is apart from the front side liquid-seal part 32b of the valve sheet member 30, and the piston part 38b at a rear side of the valve rod member 38 is brought into sliding contact with the rear side liquid-seal part 34b of the valve sheet member 30 while brought into close contact therewith to guide the manicure composition H to the applying member 16. In the above case, the space 40 through which the manicure composition H flows is completely separated off from the liquid-storing space, and therefore the manicure composition H stored in the valve mechanism is transported smoothly through an inside of the manicure-introducing tube 18 and flows out to an applying member 16 side.

In the above case, when the valve rod member 38 and the valve sheet member 30 move relatively to a shaft direction, the distance by which the second state described above is achieved is much shorter than the distances by which the first state and the third state are achieved, and it is a short distance (a distance passed through for a moment) at which a pressure in an inside of the liquid-storing space 12c can be released to the outside without allowing the manicure composition H to blob. When the valve mechanism 14 is operated with a front side of the applicator turned downward to allow the valve sheet member 30 and the valve rod member 38 to relatively move, assumed is a structure in which carried out is such a pumping action that an applying member 16 side is closed by the piston part 38a at a front side in the first state to allow the manicure composition H to flow into a space between an inner face of the valve sheet member and the valve rod member; then, in the second state, the liquid-storing space 12c is communicated from the applying member 16 to the air through the space between an inner face of the valve sheet member and the valve rod member; further, in the third state, an applying member 16 side is closed by the piston part 38b at a rear side of the valve rod member to allow the manicure composition H present in the space between an inner face of the valve sheet member and the valve rod member to flow to the applying member 16.

Accordingly, in the manicure applicator A of the above form, the liquid-storing space 12c is pressurized by an operation of the valve mechanism 14 in the first state; a pressure of the liquid-storing space 12c is released in the second state; and in the third state, the manicure composition H is allowed to flow out smoothly to the applying member 16. Consequently, the air-replacing property is very good, and even when air in the liquid-storing space 12c is expanded in a volume by a temperature rise and the like and even when a pressure of the liquid-receiving storing space 12c grows too high, blobbing of the manicure composition H by sudden flooding thereof is prevented from being brought about. After coating a nude color (translucent nail) on a whole nail, the manicure composition H of a French nail type according to the present invention is coated on an edge part of a nail part since it flows out smoothly from the applying member 16, and lines and patterns are drawn directly on a nail or drawn on a coating film of a nail enamel comprising nitrocellulose, a resin, acetate esters and the like which is coated in advance on a nail, whereby the coating is completed.

The manicure composition H of the present invention constituted in the above manner comprises at least ethanol and propylene glycol monomethyl ether as solvents, titanium oxide A having an average primary particle diameter of 200 to 400 nm, titanium oxide B having an average primary particle diameter of 10 to 80 nm, an acrylic resin, polyether-modified polydimethylsiloxane and a plasticizer, whereby provided is a manicure composition of a French nail type which has less disturbance of the line brought about by a base color and a topcoat and is quickly dried, which does not cause dew condensation on the coating film even under a moist environment for coating and has less leveling and less irregular color and which is excellent in a drying property, an adhesive property, flexibility, a masking property, a finished property, a discharge performance and a restirring property.

In conventional manicure compositions of a French nail type, when beautiful lines and patterns are drawn on an edge part of a nail, they are blurred or indistinct in the boundaries and are unsatisfactory in a drying property and a masking property in a certain case. In the present invention, however, the very excellent manicure composition of a French nail type free of blurring in the lines and disturbance in the boundaries which are brought about by a base color and a topcoat can be prepared.

EXAMPLES

Next, the present invention shall be explained in further details with reference to examples and comparative examples, but the present invention shall not be restricted by the examples shown below.

Examples 1 to 11 and Comparative Examples 1 to 7

The components were mixed and dispersed in blend compositions shown in the following Table 1 by means of a homomixer or a disper to prepare the respective manicure compositions.

The respective manicure compositions obtained in Examples 1 to 11 and Comparative Examples 1 to 7 described above were used to evaluate the respective viscosities of 25° C. at the shear rates of 3.83 ($s^{-1}$) and 383 ($s^{-1}$), a drying property, an adhesive property, flexibility, a masking property, a finished property, a discharge performance and a restirring property by the following methods. The results thereof are shown in the following Table 1.

Measuring Method of Viscosity:

The respective manicure compositions obtained were used to measure a viscosity in the prescribed shear rates at a temperature of 25° C. by means of a corn plate type viscometer (among TV-30 viscometers, an ELD type viscometer or a standard corn plate type viscometer manufactured by Tokimec Inc.).

Evaluation Method of Drying Property:

A coating film was formed on a flat test board in a constant thickness and scratched thereon by a cotton swab and the like at constant time interval, whereby a drying time of the coating film was measured to evaluate a drying property thereof according to the following evaluation criteria.

Evaluation Criteria:

1: too quick (X)

2: quick drying, good (◯)

3: a little slow (Δ)

4: too slow (X)

Evaluation Method of Flexibility:

The test was carried out according to JIS K5600-5-1 to evaluate the flexibility according to the following evaluation criteria.

Evaluation Criteria:

◯: endure bending (No crack is formed at all on the coating film)

Δ: endure bending a little (cracks are formed on a part of the coating film)

X: do not endure bending (cracks are formed on the coating film)

Evaluation Method of Masking Property:

The sample was coated on a base color, and a see-through degree of the base color was observed to evaluate the masking property according to the following evaluation criteria.

Evaluation Criteria:

◯: the base color is not seen-through at all.

Δ: the base color is seen-through a little but acceptable to use.

X: the base color is seen-through and not masked.

Evaluation Method of Finished Property:

The applicator shown in FIG. 1 was charged with the respective manicure compositions, and French nail line was drawn on an edge part of a nail to evaluate a finished property thereof according to the following evaluation criteria.

Evaluation Criteria:

◯: beautiful French nail line having no cissing is drawn readily for a short time.

Δ: French nail line is drawn as desired, though a little inferior.

X: French nail line is dirty, not smooth and cissing remarkably.

Evaluation Method of Discharge Performance:

The applicator shown in FIG. 1 was charged with the respective manicure compositions, and the content liquid was discharged to evaluate a discharge performance thereof according to the following evaluation criteria.

Evaluation Criteria:

◯: an applicable state is ready in several times of discharge actions.

Δ: a frequency of discharge actions is increased but falls in an acceptable range to use.

X: the content liquid cannot be discharged, and is difficult to discharge.

Evaluation Method of Restirring Property:

The applicator shown in FIG. 1 was charged with the respective manicure compositions and left standing still at 50° C. for one month. The prepared applicator described above was shaken with a hand to observe movement of the stirring ball, and it was evaluated according to the following criteria.

Evaluation Criteria:

◯: the stirring ball was moved by shaking once to three times.

Δ: the stirring ball was moved by shaking four to nine times.

X: the stirring ball was moved by shaking ten times or more.

TABLE 1

(whole amount: 100% by mass)

| | Example | | | | | | | | |
|---|---|---|---|---|---|---|---|---|---|
| | 1 | 2 | 3 | 4 | 5 | 6 | 7 | 8 | 9 |
| Titanium oxide A CR-50 *1 | 5.100 | 5.100 | 5.100 | 5.100 | 2.000 | 5.100 | 5.100 | 5.100 | 5.100 |
| Titanium oxide B TTO-55(A) *2 | 6.000 | 6.000 | 6.000 | 1.000 | 6.000 | 6.000 | 6.000 | 6.000 | 6.000 |
| Red No. 201 | — | 0.100 | — | — | — | — | — | — | 0.010 |
| Red No. 202 | — | — | — | 0.020 | — | — | — | — | — |
| Red No. 220 | — | — | — | — | 0.100 | — | — | — | 0.010 |
| Yellow No. 4 Al Lake | 0.018 | — | — | — | — | — | — | 0.018 | — |
| Iron blue | — | — | — | — | — | 0.020 | — | 0.020 | — |
| Red iron oxide | — | — | — | — | — | — | 0.020 | — | — |
| Nitrocellulose | 0.003 | 0.010 | — | 0.003 | 0.010 | 0.003 | 0.003 | 0.006 | 0.001 |
| Acrylic resin *3 | 9.000 | 9.000 | 9.000 | 9.000 | 9.000 | 9.000 | 9.000 | 9.000 | 9.000 |
| Polyether-modified dimethyl-polysiloxane *4 | 0.010 | 0.010 | 0.010 | 0.010 | 0.010 | 0.010 | 0.010 | 0.0005 | 0.200 |
| Plasticizer *5 | 3.000 | 3.000 | 3.000 | 3.000 | 3.000 | 0.100 | 12.000 | 3.000 | 3.000 |
| Propylene glycol monomethyl ether | 20.000 | 20.000 | 20.000 | 20.000 | 20.000 | 20.000 | 20.000 | 20.000 | 20.000 |
| Ethanol | Balance | Balance | Balance | Balance | Balance | Balance | Balance | Balance | Balance |
| Viscosity shear rate 3.83 (1/s) | 18 | 18 | 18 | 15 | 18 | 18 | 20 | 18 | 18 |
| shear rate 383 (1/s) | 18 | 18 | 18 | 15 | 18 | 18 | 20 | 18 | 18 |
| Drying property | 2 | 2 | 2 | 2 | 2 | 2 | 3 | 2 | 2 |
| Adhesive property | ○ | ○ | ○ | ○ | ○ | ○ | ○ | ○ | ○ |
| Flexibility | ○ | ○ | ○ | ○ | ○ | Δ | ○ | ○ | ○ |
| Masking property | ○ | ○ | ○ | ○ | Δ | ○ | ○ | ○ | ○ |
| Finished property | ○ | ○ | ○ | Δ | ○ | Δ | Δ | Δ | Δ |
| Discharge performance | ○ | ○ | ○ | ○ | ○ | ○ | ○ | ○ | ○ |
| Restirring property | ○ | ○ | ○ | ○ | ○ | ○ | ○ | ○ | ○ |

| | Example | | Comparative Example | | | | | | |
|---|---|---|---|---|---|---|---|---|---|
| | 10 | 11 | 1 | 2 | 3 | 4 | 5 | 6 | 7 |
| Titanium oxide A CR-50 *1 | 5.100 | 5.100 | 11.000 | — | 5.100 | 5.100 | 5.100 | 5.100 | 5.100 |
| Titanium oxide B TTO-55(A) *2 | 6.000 | 6.000 | — | 10.000 | 6.000 | 6.000 | 6.000 | 6.000 | 6.000 |
| Red No. 201 | — | — | — | — | — | — | — | — | — |
| Red No. 202 | — | — | — | — | — | — | — | — | — |
| Red No. 220 | — | — | — | — | — | — | — | — | — |
| Yellow No. 4 Al Lake | 0.018 | 0.018 | 0.018 | 0.018 | 0.018 | 0.018 | 0.018 | 0.018 | 0.018 |
| Iron blue | — | — | — | — | — | — | — | — | — |
| Red iron oxide | — | — | — | — | — | — | — | — | — |
| Nitrocellulose | 0.003 | 0.003 | 0.003 | 0.003 | 0.003 | 0.003 | 0.003 | 0.003 | 0.003 |
| Acrylic resin *3 | 0.500 | 30.000 | 9.000 | 9.000 | — | 9.000 | 9.000 | 9.000 | 9.000 |
| Polyether-modified dimethyl-polysiloxane *4 | 0.010 | 0.010 | 0.010 | 0.010 | 0.010 | 0.010 | 0.010 | — | 0.010 |
| Plasticizer *5 | 3.000 | 3.000 | 3.000 | 3.000 | 3.000 | — | 3.000 | 3.000 | 3.000 |
| Propylene glycol monomethyl ether | 20.000 | 20.000 | 20.000 | 20.000 | 20.000 | 20.000 | — | 20.000 | Balance |
| Ethanol | Balance | Balance | Balance | Balance | Balance | Balance | Balance | Balance | — |
| Viscosity shear rate 3.83 (1/s) | 10 | 80 | 20 | 15 | 5 | 18 | 15 | 18 | 25 |
| shear rate 383 (1/s) | 10 | 50 | 20 | 15 | 5 | 18 | 15 | 18 | 25 |
| Drying property | 2 | 2 | 2 | 2 | 2 | 2 | 1 | 2 | 4 |
| Adhesive property | Δ | ○ | ○ | ○ | x | ○ | ○ | ○ | Δ |
| Flexibility | ○ | Δ | ○ | ○ | ○ | x | ○ | ○ | ○ |
| Masking property | ○ | ○ | ○ | x | ○ | ○ | ○ | ○ | ○ |
| Finished property | Δ | Δ | x | x | x | Δ | x | x | x |
| Discharge performance | Δ | Δ | ○ | ○ | Δ | ○ | x | ○ | ○ |
| Restirring property | Δ | Δ | ○ | ○ | x | ○ | ○ | ○ | ○ |

The remarks *1 to *5 in Table 1 described above show the followings.
*1: average primary particle diameter: 250 nm, manufactured by Ishihara Sangyo Co., Ltd.
*2: average primary particle diameter: 30 to 50 nm, manufactured by Ishihara Sangyo Co., Ltd.
*3: alkyl acrylate copolymer (Luvimer 100P, manufactured by BASF AG.)
*4: PEG-12 Dimeticone (SH3775M, manufactured by Dow Corning Toray Co., Ltd.)
*5: acetyl triethyl citrate As apparent from the results shown in Table 1 described above, it has become clear that the manicure compositions prepared in Examples 1 to 11 according to the present invention are manicure compositions of a French nail type which are excellent in a drying property, an adhesive property, flexibility, a masking property, a finished property, a discharge performance and a restirring property as compared with the manicure compositions prepared in Comparative Examples 1 to 7 falling outside the ranges of the present invention.

To observe individually the Comparative examples, Comparative Examples 1 and 2 are cases in which titanium oxides having different average particle diameters which fall in the ranges of the present invention are not used in combination; Comparative Example 3 is a case in which the acrylic resin is not contained; Comparative Example 4 is a case in which the plasticizer is not contained; Comparative Examples 5 and 7 are cases in which the solvents are not used in combination; and Comparative Example 6 is a case in which polyether-modified polydimethylsiloxane is not contained. It has been found that the effects of the present invention can not be exhibited in the above cases.

INDUSTRIAL APPLICABILITY

The manicure compositions of the present invention are manicure compositions which are suited to a French nail type.

What is claimed is:

1. A manicure composition comprising at least ethanol and propylene glycol monomethyl ether as solvents, 1 to 20% by mass of block-shaped particulate titanium oxide A having an average primary particle diameter of 200 to 400 nm, block-shaped particulate titanium oxide B having an average primary particle diameter of 10 to 80 nm, an acrylic resin, polyether-modified polydimethylsiloxane and a plasticizer.

2. The manicure composition as described in claim 1, wherein assuming that a content of the block-shaped particulate titanium oxide A having an average primary particle diameter of 200 to 400 nm is 1, a blend ratio of the block-shaped particulate titanium oxide B having an average primary particle diameter of 10 to 80 nm is 0.5 to 1.5 in terms of a mass ratio.

3. The manicure composition as described in claim 1, wherein assuming that a content of propylene glycol monomethyl ether described above is 1, a blend ratio of ethanol is 1 to 50 in terms of a mass ratio.

4. The manicure composition as described in claim 1, wherein a viscosity at a shear rate of 3.83 $(s^{-1})$ is 10 to 40 (mPa·s) at 25° C., and a viscosity at a shear rate of 383 $(s^{-1})$ is 10 to 30 (mPa·s).

5. The manicure composition as described in claim 2, wherein assuming that a content of propylene glycol monomethyl ether described above is 1, a blend ratio of ethanol is 1 to 50 in terms of a mass ratio.

6. The manicure composition as described in claim 5, wherein a viscosity at a shear rate of 3.83 $(a^{-1})$ is 10 to 40 (mPa·s) at 25° C., and a viscosity at a shear rate of 383 $(s^{-1})$ is 10 to 30 (mPa·s).

* * * * *